United States Patent
Ido (10) Patent No.: US 6,980,919 B2
(45) Date of Patent: Dec. 27, 2005

(54) WALKING CONDITION DETERMINING DEVICE AND METHOD

(75) Inventor: Tetsuya Ido, Wako (JP)

(73) Assignee: Honda Giken Kogyo Kabushiki Kaisha, Tokyo (JP)

(*) Notice: Subject to any disclaimer, the term of this patent is extended or adjusted under 35 U.S.C. 154(b) by 0 days.

(21) Appl. No.: 10/492,075

(22) PCT Filed: Aug. 23, 2002

(86) PCT No.: PCT/JP02/08529

§ 371 (c)(1), (2), (4) Date: Apr. 8, 2004

(87) PCT Pub. No.: WO03/032833

PCT Pub. Date: Apr. 24, 2003

(65) Prior Publication Data

US 2004/0246769 A1 Dec. 9, 2004

(30) Foreign Application Priority Data

Oct. 16, 2001 (JP) .............................. 2001-318349

(51) Int. Cl.$^7$ ......................... G06F 15/00; G06F 19/00
(52) U.S. Cl. ..................................... 702/150; 700/245
(58) Field of Search ......................... 702/150; 901/1; 700/245

(56) References Cited

U.S. PATENT DOCUMENTS

| | | | |
|---|---|---|---|
| 6,289,265 B1 * | 9/2001 | Takenaka et al. ........... | 700/245 |
| 6,301,524 B1 * | 10/2001 | Takenaka ..................... | 700/245 |
| 6,697,709 B2 * | 2/2004 | Kuroki et al. ............... | 700/245 |
| 6,741,911 B2 * | 5/2004 | Simmons ..................... | 700/245 |
| 6,802,382 B2 * | 10/2004 | Hattori et al. ............... | 180/8.6 |
| 6,816,753 B2 * | 11/2004 | Sakamoto et al. .......... | 700/245 |
| 6,832,131 B2 * | 12/2004 | Hattori et al. ............... | 700/245 |
| 6,832,132 B2 * | 12/2004 | Ishida et al. ................. | 700/245 |
| 6,850,818 B2 * | 2/2005 | Sabe et al. ................... | 700/257 |
| 6,876,903 B2 * | 4/2005 | Takenaka ..................... | 700/245 |

(Continued)

FOREIGN PATENT DOCUMENTS

JP 07-163607 6/1995

(Continued)

OTHER PUBLICATIONS

Sachiko Hisashita et al., "Nichijo Seikatsu ni okeru Jokashi Undo no Keisoku", Human Interface, Feb. 16, 1999, vol. 1, No. 1, pp. 53 to 56.

(Continued)

Primary Examiner—John Barlow
Assistant Examiner—Toan M. Le
(74) Attorney, Agent, or Firm—Rankin, Hill, Porter & Clark LLP (57) ABSTRACT

A device and a method that permit easy and accurate determination of a walking condition regardless of differences in foot landing points on soles or lengths of legs of a walker are provided. According to this device, a measuring device measures a parameter indicating a displacement speed or a displacement acceleration of a bottom end portion of one leg with respect to a bottom end portion of the other leg of the walker. A first storage device stores patterns of plots corresponding to parameters and walking conditions of the walker. A generating device generates plots defined in the determination space by parameters measured by the measuring device. A determining device determines walking conditions of the walker on the basis of the patterns of the plots stored and retained in conjunction with the walking conditions by the first storage device and the patterns of the plots generated by the generating device.

10 Claims, 4 Drawing Sheets

U.S. PATENT DOCUMENTS 6,898,485 B2 * 5/2005 Kuroki et al. .............. 700/245
6,901,313 B2 * 5/2005 Mori et al. ................. 700/245
6,904,334 B2 * 6/2005 Asano et al. ............... 700/245

FOREIGN PATENT DOCUMENTS

| JP | 11-347020 | 12/1999 |
|---|---|---|
| JP | 2000-325329 | 11/2000 |
| JP | 2001-108479 | 4/2001 |

OTHER PUBLICATIONS

Goru Nebuya et al., "Kado Sokudo oyobi Kasokudo Censer o Shiyo shita . . . ", BPES2000, Oct. 13, 2000, pp. 233 to 236.

* cited by examiner

WALKING CONDITION DETERMINING DEVICE AND METHOD

BACKGROUND OF THE INVENTION

1. Technical Field

The present invention relates to a device and a method for determining a walking condition of a walker having a plurality of legs.

2. Description of Related Art

When a device for aiding a person with deteriorated muscle strength in walking is used, it is necessary to accurately determine a walking condition, that is, whether the person is walking on a level ground, walking up or down stairs, etc. in order to properly aid the walking by the device. For this purpose, Japanese Unexamined Patent Publication No. 7-163607, for example, has proposed a method for determining a walking condition on the basis of pressures applied to soles of a walker measured by pressure sensors. Furthermore, Japanese Unexamined Patent Publication No. 2000-325329, for example, has proposed a method for determining a walking condition on the basis of angles of legs of a walker.

However, according to the determining method based on the pressures applied to soles, portions of the soles where the pressure sensors are provided may not touch stair steps especially when a walker is going up or down stairs, and walking conditions may be erroneously determined. For instance, there are cases where the walker lands on a stair at his or her tiptoes, whereas the pressure sensors are provided at their heels. Furthermore, distribution of pressures applied to soles varies, depending upon the shapes of soles of footwear, so that walking conditions may also be erroneously determined. If footwear having pressures sensors provided in its soles is used, then the pressure sensors and an arithmetic processing unit or the like for determining walking conditions must be connected or disconnected through communication lines or electric wires each time the footwear is attached or detached. This may cause the walker to feel bothersome.

According to the determining method based on the angles of legs, walking conditions may not be accurately determined, depending on lengths of the legs of a walker. For instance, when walkers climb the same stairs, the extent to which their thighs are raised for walking differs according to the length of their legs. As a result, it may be erroneously determined that a walker is climbing stairs if the walker is short, while it may be erroneously determined that the walker is walking on a level ground if the walker is tall.

Especially in the walk aiding device, erroneous determination of walking conditions leads to excessive or inadequate aiding power imparted to a walker, adversely affecting the walking.

Accordingly, the present invention has been made with a view toward solving the problems described above by providing a device and a method that allow walking conditions to be determined easily and accurately, regardless of differences in landing spots on soles or in length of legs of walkers.

BRIEF SUMMARY OF THE INVENTION

A walking condition determining device in accordance with the present invention for solving the problems described above is characterized by being equipped with a measuring means for measuring a parameter that indicates a displacement speed or a displacement acceleration of a bottom end portion of one leg in relation to a bottom end portion of the other leg of the aforesaid walker, a first storage means for storing a pattern of a plot in a determination space that corresponds to the parameter and a walking condition of the walker such that they are associated with each other, a generating means for generating a plot defined in the determination space by the parameter measured by the measuring means, and a determining means for determining a walking condition of the walker on the basis of the association relationship stored and retained by the first storage means and the plot generated by the generating means.

A walking condition determining method in accordance with the present invention for solving the problems described above is characterized by including a measuring step for measuring a parameter that indicates a displacement speed or a displacement acceleration of a bottom end portion of one leg in relation to a bottom end portion of the other leg of the aforesaid walker, an establishing step for establishing an association relationship between a pattern of a plot in a determination space associated with the parameter and a walking condition of the walker, a generating step for generating a plot defined in the determination space by the parameter measured in the measuring step, and a determining step for determining a walking condition of the walker on the basis of the association relationship established in the establishing step and the plot generated in the generating step.

The displacement speed or the displacement acceleration of the bottom end portion of one leg in relation to the bottom end portion of the other leg that is measured in the present invention depends heavily on a walking place, e.g., a level ground or stairs, and hardly depends on differences in landing spots on soles or the length of legs of a walker. For this reason, a pattern of a plot in a determination space defined by a parameter indicating the displacement amount remains substantially the same under the same walking condition, independently of the differences in landing spots on soles or the length of legs of a walker. In addition, the present invention does not involve bothersome connection or disconnection of wiring required each time special footwear for pressure measurement is attached or detached. Thus, the present invention makes it possible to easily and accurately determine a walking condition on the basis of a plot pattern in a determination space regardless of differences in landing spots on soles or length of legs of a walker.

The first storage means stores a plot configuration pattern in the determination space as the plot pattern. The determining means determines a walking condition of the walker on the basis of the determination whether or not the configuration pattern stored and retained in by the first storage means is identical or similar to a generated plot configuration pattern generated by the generating means.

According to the present invention, a walking condition can be determined on the basis of a "configuration pattern," that is, a pattern of a plotted configuration drawn in the determination space.

Furthermore, the first storage means stores an existence plot pattern in the determination space as the plot pattern, and the determining means determines a walking condition of the walker on the basis of whether or not the existence pattern stored and retained by the first storage means is identical or similar to an existence plot pattern generated by the generating means.

According to the present invention, it is possible to determine a walking condition on the basis of an "existence pattern" showing regions in the determination space wherein plots exist.

The measuring means is provided with a first measuring means for measuring, as a first parameter, an angular velocity of a slope angle formed with respect to a horizontal plane by a vector directed from a bottom end portion of one leg to a bottom end portion of the other leg of the walker, and a second measuring means for measuring an angular acceleration of the slope angle as a second parameter. The determining means determines that the walker is in a normal walking condition if a plot in the determination space indicates an existence pattern in which a total of second parameters when the first parameter reaches zero in one walking period is below a predetermined absolute value, whereas it determines that the walker is in a slope walking condition if the plot indicates an existence pattern in which the total is the predetermined absolute value or more.

Furthermore, if the determining means determines that the walker is in the slope walking condition, then it determines that the walker is in an ascending walking condition if a plot in the determination space indicates an existence pattern in which the total is negative, while it determines that the walker is in a descending walking condition if the plot indicates an existence pattern in which the total is positive.

According to the present invention, regarding an angular velocity and an angular acceleration of the slope angle that are denoted by first and second parameters and reflected in an existence pattern of a plot in a determination space, a walking condition can be accurately determined on the basis of knowledge obtained by the present inventors, which will be discussed hereinafter.

The "normal walking condition" means a condition in which a walker is walking on a level ground, a gentle slope, or a stairs with small step height differences. The "slope walking condition" means a condition in which a walker is walking a steep slope or stairs with large step height differences. Here, whether a sloping road is gentle or steep, or whether stairs have small or large step height differences is determined by setting the "predetermined absolute value."

The present invention is characterized by being equipped with a second storage means for storing joint-to-joint distances of the legs of the walker and an angle sensor for measuring joint angles of the legs, and a first and a second measuring means measure first and second parameters on the basis of the joint-to-joint distances stored and retained by the second storage means and joint angles measured by the angle sensor.

The present invention makes it possible to measure joint-to-joint distances of the legs and joint angles and the first and second parameters on the basis of a simple geometric speculation, as will be discussed hereinafter.

The determining means determines a walking condition of the walker on the basis of a series of plots generated by the generating means over a semi-walking period in an immediately preceding period of the walker.

Furthermore, the present invention is characterized by being equipped with a semi-walking period measuring means for measuring a semi-walking period of the walker on the basis of a timing at which the first parameter measured by the first measuring means reaches zero during a walking period.

According to the present invention, a walking condition of a walker can be determined on the basis of a plot pattern for each semi-walking period in a determination space.

DETAILED DESCRIPTION OF THE INVENTION

A walking condition determining device and method in accordance with the present invention will be explained in conjunction with accompanying drawings. A walking condition determining device 1 shown in FIG. 1 constitutes a part of a walk aiding apparatus 2 used by being attached to a human being, who is a walker.

Figure 1:
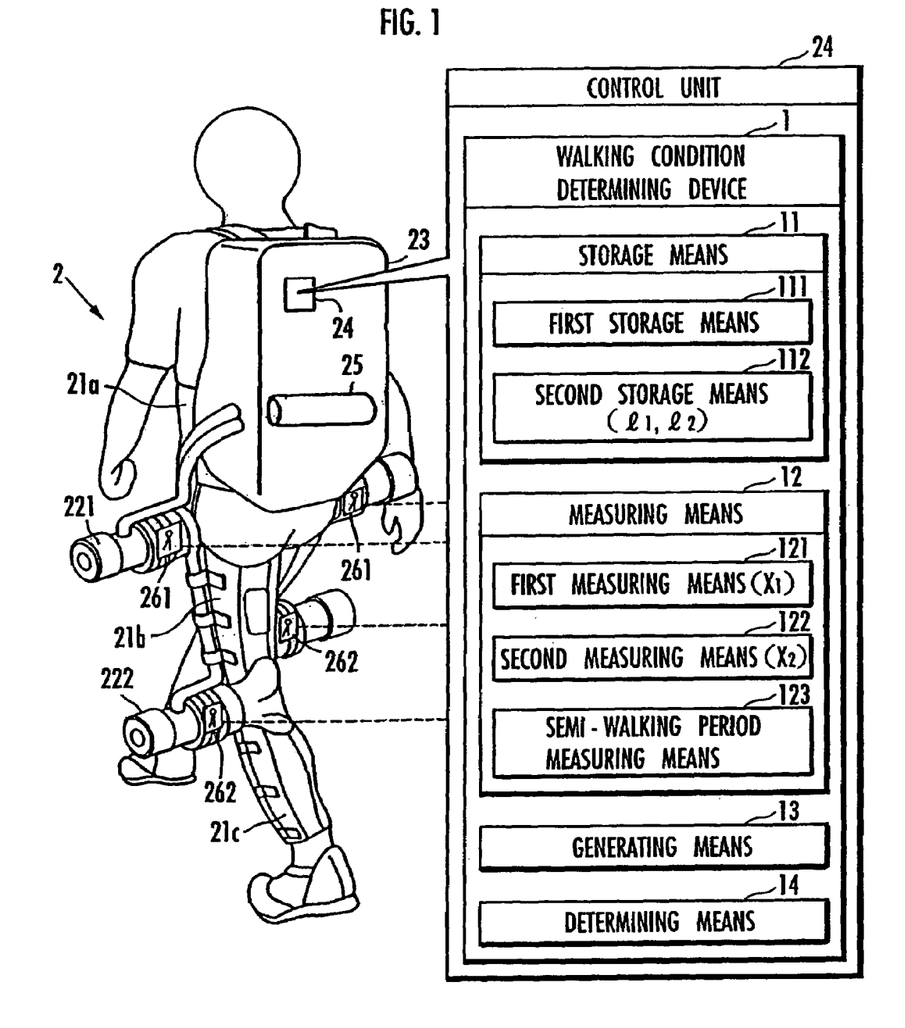
FIG. 1 is a construction explanatory diagram of a walking condition determining device according to the present embodiment.

The walk aiding apparatus 2 is provided with supporters 21a, 21b, and 21c attached to the abdomen, thighs, and shins of the walker, a first actuator 221 located at the waist of the walker to impart torque about hip joints through the intermediary of the supporters 21a and 21b, a second actuator 222 located at knees of the walker to impart torque about knee joints through the intermediary of the supporters 21b and 21c, a control unit 24 accommodated in a backpack 23 on the back of the walker to control operations or the like of the actuators 221 and 222, and a battery 25 also accommodated in the backpack 23 to supply power to the actuators 221 and 222.

The walk aiding apparatus 2 is further provided with first angle sensors 261 located on the left and right sides of the waist of the walker to measure the angles of the left and right hip joints $\theta_{1L}$ and $\theta_{1R}$ and second angle sensors 262 located on the left and right knees of the walker to measure the angles of the left and right knee joints $\theta_{2L}$ and $\theta_{2R}$.

Figure 3:
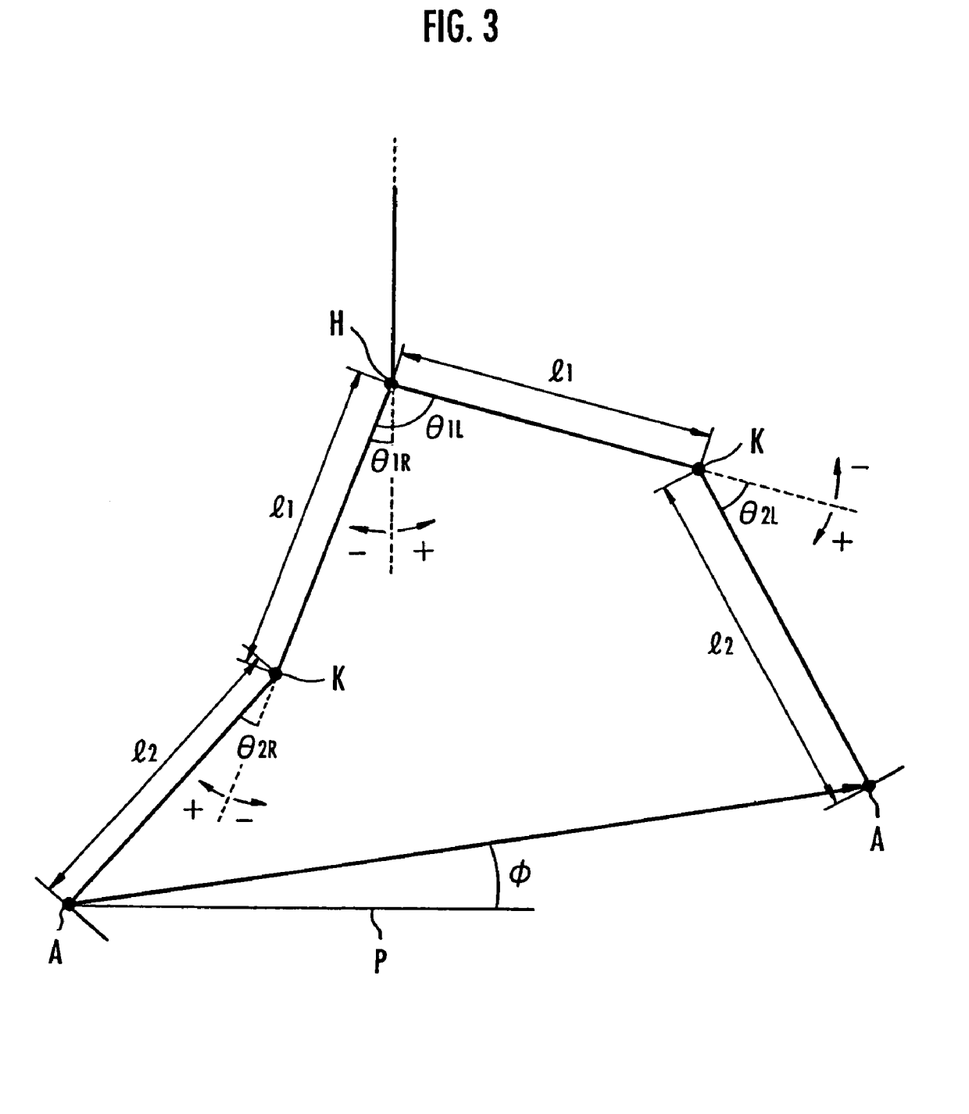
FIG. 3 is an explanatory diagram of a method of measuring first and second parameters according to the present embodiment.

According to a leg model shown in FIG. 3, the angles of the left and right hip joints $\theta_{1L}$ and $\theta_{1R}$ are the angles formed by thighs having a length $l_1$ with respect to a vertical plane that includes a hip joint H. The angles are defined as positive angles if the thighs are ahead of the plane, while they are defined as negative if the thighs are behind the plane. The angles of the left and right knee joints $\theta_{2L}$ and $\theta_{2R}$ are the angles formed by the left and right shins having a length $l_2$ with respect to a plane that includes the left and right thighs. The angles are defined as negative angles if the shins are ahead of the plane, while they are defined as positive if the shins are behind the plane.

The walking condition determining device 1 is equipped with a storage means 11, a measuring means 12, a generating means 13, and a determining means 14 that partly constitute the control unit 24.

Figure 4:
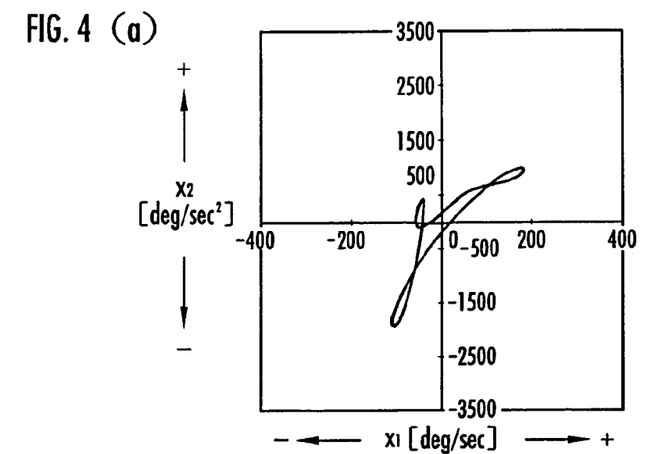
FIG. 4 is an explanatory diagram of walking condition determination results in the present embodiment.

The storage means 11 constructed of a ROM, a RAM, and the like is equipped with a first storage means 111 for storing plot existence patterns (refer to FIG. 4) in the determination space and walking conditions of the walker such that they are associated with each other, and a second storage means 112 for storing a distance $l_1$ between a hip joint and a knee joint of the walker and a distance $l_2$ between a knee joint and a foot joint of the walker, the distances being measured in advance.

The measuring means 12 is provided with a first measuring means 121, a second measuring means 122, and a semi-walking period measuring means 123.

The first measuring means 121 includes, as components, a first angle sensor 261, a second angle sensor 262, and a second storage means 112. An angular velocity (a first parameter) $x_1$ of a slope angle $\phi$ (refer to FIG. 3), which will be discussed hereinafter, is measured on the basis of the angles of the left and right hip joints $\theta_{1L}$ and $\theta_{1R}$ and the left and right knee joint angles $\theta_{2L}$ and $\theta_{2R}$ of the walker that are measured by the first and second angle sensors 261 and 262, and the joint-to-joint distances $l_1$ and $l_2$ stored and retained in the second storage means 112.

Similarly, the second measuring means 122 includes, as components, a first angle sensor 261, a second angle sensor 262, and a second storage means 112. An angular acceleration (a second parameter) $x_2$ of a slope angle $\phi$ (refer to FIG. 3), which will be discussed hereinafter, is measured on the basis of the angles of the left and right hip joints $\theta_{1L}$ and $\theta_{1R}$ and the angles of the left and right knee joints $\theta_{2L}$ and $\theta_{2R}$ of the walker that are measured by the first and second angle sensors 261 and 262, and the joint-to-joint distances $l_1$ and $l_2$ stored and retained in the second storage means 112.

The semi-walking period measuring means 123 measures a semi-walking period of the walker on the basis of a timing at which the first parameter $x_1$ measured by the first measuring means 121 reaches zero during a walking period.

The generating means 13 constructed of a CPU, a signal input/output circuit, a RAM, a ROM, etc. generates plots (plotting data) in a two-dimensional determination space associated with the first parameter $x_1$ and the second parameter $x_2$.

Similarly, the determining means 14 constructed of a CPU, a signal input/output circuit, the first storage means 111, etc. determines the walking condition of the walker on the basis of a plot existence pattern generated by the generating means 13 and a plot pattern stored and retained by the first storage means 111, as will be discussed hereinafter.

Functions of a walking condition determining device 1 will now be explained in conjunction with FIG. 2 to FIG. 5.

Figure 2:
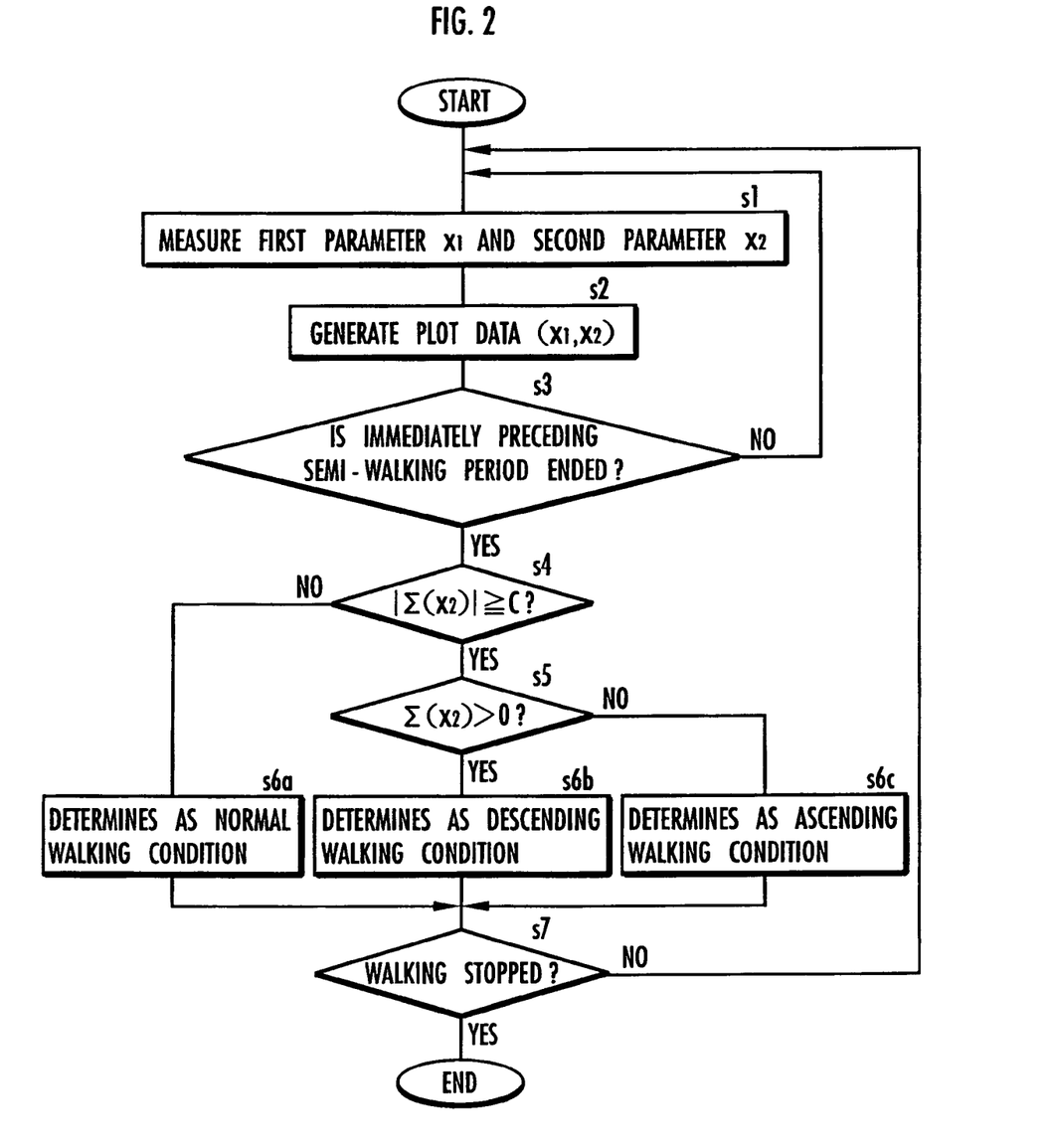
FIG. 2 is an explanatory diagram showing a procedure of a walking condition determining method according to the present embodiment.

First, the first and second measuring means 121 and 122 measure the first and second parameters $x_1$ and $x_2$ (s1 shown in FIG. 2). The measurement is performed according to expressions (1) and (2) below, using the hip-to-knee and knee-to-foot joint distances $l_1$ and $l_2$ of the walker stored and retained by the second storage means 112, and the left and right hip and knee joint angles $\theta_{1L}$, $\theta_{1R}$ and $\theta_{2L}$, $\theta_{2R}$ measured by the first and second angle sensors 261 and 262.

$$X_1 = d\phi/dt \qquad (1)$$

$$X_2 = d^2\phi/dt^2 \qquad (2)$$

where $\phi$ is defined as an absolute value of a slope angle formed by a vector (thick arrow) directed from a right foot joint (a bottom end portion of one leg) to a left foot joint (a bottom end portion of the other leg) with respect to a horizontal plane p, as shown in FIG. 3. The slope angle $\phi$ is represented by expression (3) given below based on an elementary geometric speculation, using the leg model shown in FIG. 3, in which a hip joint H and a knee joint K are connected by a rigid bar having the length $l_1$, and a knee joint K and a foot joint A are connected by a rigid bar having the length $l_2$.

$$\phi = \tan^{-1}[[l_1\cos\theta_{1L} + l_2\cos(\theta_{1L} - \theta_{2L}) - l_1\cos\theta_{1R} - l_2\cos(\theta_{1R} - \theta_{2R})] \qquad (3)$$
$$/[l_1\sin\theta_{1L} + l_2\sin(\theta_{1L} - \theta_{2L}) - l_1\sin\theta_{1R} - l_2\sin(\theta_{1R} - \theta_{2R})]]$$

Next, the generating means 13 generates a "plot" defined by the first and second parameters ($x_1$, $x_2$) measured by the first and second measuring means 121 and 122 in the two-dimensional "determination space" (s2 in FIG. 2).

The semi-walking period measuring means 123 determines whether the immediately preceding semi-walking period has ended on the basis of a timing at which the first parameter $x_1$ measured by the first measuring means 121 reaches zero (s3 in FIG. 2). Until the determination is made (NO in s3 in FIG. 2), the measurement of the first and second parameters $x_1$ and $x_2$ (s1 in FIG. 2) and the generation of a plot (s2 in FIG. 2) are repeated. A track on a plot ($x_1$, $x_2$) drawn in one walking period is represented by the curves shown in FIG. 4(a) to FIG. 4(c).

If it is determined that the immediately preceding semi-walking period is finished (YES in s3 in FIG. 2), then the determining means 14 determines a walking condition. For this determination, the existence patterns stored and retained in association with walking conditions by the first storage means 111, that is, the patterns indicating the regions in the determination space wherein plots exist are used (refer to FIG. 4). To be more specific, an existence pattern in which a sum of the second parameters $x_2$ (hereinafter denoted as "$\Sigma x_2$") when the first parameter $x_1$ reaches zero during one walking period is below a predetermined absolute value c is associated with the "normal walking condition". An existence pattern in which the sum $\Sigma x_2$ is the predetermined absolute value c or more and positive is associated with the "descending walking condition." Furthermore, an existence pattern in which the sum $\Sigma x_2$ is the predetermined absolute value c or more and negative is associated with the "ascending walking condition." The association is based on knowledge obtained from results of experiments carried out by the inventors of the present application.

To determine a walking condition, it is first determined whether the pattern is the existence pattern in which an absolute value of the sum $|\Sigma x_2|$ is below the predetermined absolute value c (s4 in FIG. 2). If it is determined to be an existence pattern in which the sum $\Sigma x_2$ of the second parameter $x_2$ is relatively small and smaller than the predetermined absolute value c when the first parameter $x_1$ takes zero twice in succession, as indicated by the black dots in FIG. 4(a) (NO in s4 in FIG. 2), then it is determined that the walker is in the "normal walking condition" (s6a in FIG. 2).

Meanwhile, if it is determined to be an existence pattern in which the absolute value of the sum $|\Sigma x_2|$ is the predetermined absolute value c or more (YES in s4 in FIG. 2), then whether the sum $\Sigma x_2$ is positive or negative is determined (s5 in FIG. 2). If $\Sigma x_2$ is determined to be a positive existence pattern, then it is determined that the walker is in the "descending walking condition" (s6b in FIG. 2). If $\Sigma x_2$ is determined to be a negative existence pattern, then it is determined that the walker is in the "ascending walking condition" (s6c in FIG. 2).

The walking condition is determined for each semi-walking period (s1 to s6 in FIG. 2) unless the walker stops walking (NO in s7 in FIG. 2). Then, based on the determination of the walking condition, the control unit 24 determines torque to be applied to the legs, and the torque is applied through the intermediary of the first and second actuators 221 and 222.

As described above, the first and second parameters $x_1$ and $x_2$ denote the angular velocity and angular acceleration of the slope angle formed by the vector (thick arrow) directed from the right foot joint (the bottom end portion of one leg) to the left foot joint (the bottom end portion of the other leg) with respect to the horizontal plane p, as shown in FIG. 3. These angular velocity and angular acceleration primarily depend on the level of changes of landing positions of the right and left legs of the walker, and hardly depend on the differences in landing spots on soles or in the length of legs.

Thus, according to the device 1, the existence pattern of a plot defined by the first and second parameters $x_1$ and $x_2$ will be substantially the same in the determination space when the walking condition is the same, irrespectively of individual differences among walkers or walking speed (FIG. 4(a) to FIG. 4(c)). Moreover, the device 1 involves no special footwear that includes pressure sensors for determining walking conditions and has to be attached and detached, which requires connection and disconnection of various types of wires. Hence, walking conditions can be determined easily and accurately on the basis of plots ($x_1$, $x_2$) in the determination space regardless of differences in landing spots in the soles of walkers or differences in the length of legs.

In the present embodiment, the walker is a human being. However, in other embodiments, the walkers may be various types of two- or four-legged walking animals, humanoid robots or zoomorphic robots.

In the present embodiment, the two parameters $x_1$ and $x_2$ have been measured as the parameters representing a positional relationship of foot joints with respect to hip joints, and walking conditions have been determined on the basis of the plots in the two-dimensional determination space. As another embodiment, one parameter may be measured as the aforesaid parameter, and a walking condition may be determined on the basis of a plot in a one-dimensional determination space. Alternatively, three or more parameters may be measured, and a walking condition may be determined on the basis of a pattern of a plot in a determination space of three or more dimensions.

In the present embodiment, walking conditions have been determined, using existence patterns based on the positions of plots (0, $x_2$) providing intersections with the axis of the second parameter $x_2$. In another embodiment, walking conditions may be determined, using existence patterns based on the presence of plots ($x_1$, $x_2$) in predetermined regions of a determination space.

As yet another embodiment, walking conditions may be determined, using plot configuration patterns drawn in a determination space. For example, it may be determined as the normal walking condition if the configuration of a plot for one walking period shows one intersection in a third quadrant, as shown in FIG. 4(a), or as the descending walking condition if the configuration indicates a bend at an acute angle in the third quadrant, as shown in FIG. 4(b), or as the ascending walking condition if the configuration indicates a smooth curve without an intersection in the third quadrant, as shown in FIG. 4(c).

In the present embodiment, three different walking conditions associated with the three existence patterns of the plots in the determination space have been determined (refer to s6a to 6c in FIG. 2, and FIG. 4(a) to 4(c)). As another embodiment, more walking conditions may be determined on the basis of more existence patterns. For instance, more detailed walking conditions can be determined if steepness of hills or difference in step height of stairs is divided into more steps. This allows the control unit 24 of the walk aiding apparatus 2 to properly determine torque to be imparted to a walker on the basis of determination of more detailed walking conditions.

In the present embodiment, the walking conditions have been determined each time the semi-walking period elapses (refer to s3 in FIG. 2). As another embodiment, however, walking conditions may be steadily determined. For example, it may be determined that a walker is in the "descending walking condition" immediately after it is determined that a plot (0, $x_2$) is in a region $\{x_2 \geq c' > c\}$ of a determination space, or it may be determined that a walker is in the "ascending walking condition" immediately after it is determined that the plot is in a region $\{x_2 \leq -c' < -c\}$ of the determination space.

What is claimed is:

1. A walking condition determining device for determining a walking condition of a walker having a plurality of legs, comprising:
    a measuring means for measuring a parameter that indicates a displacement speed or a displacement acceleration of a bottom end portion of one leg in relation to a bottom end portion of the other leg of the walker;
    a first storage means for storing a pattern of a plot in a determination space associated with the parameter and a walking condition of the walker such that they are associated with each other;
    a generating means for generating a plot defined in the determination space by the parameter measured by the measuring means; and
    a determining means for determining a walking condition of the walker on the basis of the association relationship stored and retained by the first storage means and the plot generated by the generating means.

2. The device according to claim 1, wherein the first storage means stores a configuration pattern of a plot in the determination space as the plot pattern, and the determining means determines a walking condition of the walker on the basis of the determination whether or not the configuration pattern stored by the first storage means is identical or similar to a configuration pattern of the plot generated by the generating means.

3. The device according to claim 1, wherein the first storage means stores an existence pattern of a plot in the determination space as the plot pattern, and the determining means determines a walking condition of the walker on the basis of whether or not the existence pattern stored and retained by the first storage means is identical or similar to an existence pattern of the plot generated by the generating means.

4. The device according to claim 3, wherein the measuring means comprises a first measuring means for measuring, as a first parameter, an angular velocity of a slope angle formed with respect to a horizontal plane by a vector directed from a bottom end portion of one leg to a bottom end portion of the other leg of the walker, and a second measuring means for measuring an angular acceleration of the slope angle as a second parameter, and
    the determining means determines that the walker is in a normal walking condition if a plot in the determination space shows an existence pattern in which a total of second parameters when the first parameter reaches zero during one walking period is below a predetermined absolute value, whereas it determines that the walker is in a slope walking condition if the plot shows an existence pattern in which the total is the predetermined absolute value or more.

5. The device according to claim 4, wherein when the determining means determines that the walker is in the slope walking condition, it determines that the walker is in an ascending walking condition if a plot in the determination space shows an existence pattern in which the total is negative, while it determines that the walker is in a descending walking condition if the plot shows an existence pattern in which the total is positive.

6. The device according to claim 5, further comprising a second storage means for storing joint-to-joint distances of legs of the walker and an angle sensor for measuring joint angles of the legs, wherein the first and the second measuring means measure the first and second parameters on the basis of the joint-to-joint distances of the legs stored by the second storage means and joint angles measured by the angle sensor.

7. The device according to claim 4, further comprising a second storage means for storing joint-to-joint distances of legs of the walker and an angle sensor for measuring joint angles of the legs, wherein the first and the second measuring means measure the first and second parameters on the basis of the joint-to-joint distances of the legs stored by the second storage means and joint angles measured by the angle sensor.

8. The device according to claim 1, wherein the determining means determines a walking condition of the walker on the basis of a series of plots generated by the generating means over an immediately preceding semi-walking period of the walker.

9. The device according to claim 8, further comprising a semi-walking period measuring means for measuring the semi-walking period of the walker on the basis of a timing at which the first parameter measured by the first measuring means reaches zero during a walking period.

10. A walking condition determining method for determining a walking condition of a walker having a plurality of legs, comprising:

a measurement step for measuring a parameter that indicates a displacement speed or a displacement acceleration of a bottom end portion of one leg in relation to a bottom end portion of the other leg of the walker;

an establishing step for establishing an association relationship between a pattern of a plot in a determination space corresponding to the parameter and a walking condition of the walker;

a generating step for generating a plot defined in the determination space by the parameter measured in the measurement step; and a determining step for determining a walking condition of the walker on the basis of the association relationship established in the establishing step and the plot generated in the generating step.

* * * * *